US008900327B2

(12) United States Patent  
Bertels et al.

(10) Patent No.: US 8,900,327 B2
(45) Date of Patent: Dec. 2, 2014

(54) PROSTHETIC JOINT

(75) Inventors: Thomas Bertels, Duderstadt (DE);
Tobias Groβ, Günterode (DE)

(73) Assignee: Otto Bock Healthcare GmbH,
Duderstadt (DE)

( * ) Notice: Subject to any disclaimer, the term of this patent is extended or adjusted under 35 U.S.C. 154(b) by 679 days.

(21) Appl. No.: 11/743,312

(22) Filed: May 2, 2007

(65) Prior Publication Data

US 2007/0260328 A1 Nov. 8, 2007

(30) Foreign Application Priority Data

May 3, 2006 (DE) .......................... 10 2006 020 777

(51) Int. Cl.
*A61F 2/68* (2006.01)
*A61F 2/58* (2006.01)
*A61F 2/62* (2006.01)
*A61F 2/50* (2006.01)
*A61F 2/76* (2006.01)
*A61F 2/78* (2006.01)
*A61F 2/30* (2006.01)

(52) U.S. Cl.
CPC ......... *A61F 2/585* (2013.01); *A61F 2220/0041* (2013.01); *A61F 2002/5009* (2013.01); *A61F 2/76* (2013.01); *A61F 2002/5075* (2013.01); *A61F 2002/6854* (2013.01); *A61F 2002/6818* (2013.01); *A61F 2/68* (2013.01); *A61F 2002/5018* (2013.01); *A61F 2002/7875* (2013.01); *A61F 2002/5043* (2013.01); *A61F 2002/30438* (2013.01)
USPC ............................................. 623/61; 623/39

(58) Field of Classification Search
USPC ...................... 623/38, 51, 47, 61; 602/20–29; 403/1–410
See application file for complete search history.

(56) References Cited

U.S. PATENT DOCUMENTS

| 2,706,296 | A | * | 4/1955 | Fletcher et al. ................. 623/64 |
| 2,812,961 | A |   | 11/1957 | Brown et al. |
| 3,692,161 | A |   | 9/1972 | Katsuren et al. |
| 4,636,221 | A | * | 1/1987 | Kemp ............................. 623/59 |
| 4,846,842 | A |   | 7/1989 | Connolly et al. |
| 5,246,465 | A | * | 9/1993 | Rincoe et al. ................... 623/39 |
| 5,888,235 | A | * | 3/1999 | Jacobsen et al. ............... 623/58 |
| 5,913,901 | A | * | 6/1999 | Lacroix .......................... 623/47 |
| 7,144,430 | B2 | * | 12/2006 | Archer et al. .................. 623/61 |
| 7,517,330 | B2 | * | 4/2009 | Deharde et al. ................ 602/16 |
| 7,914,587 | B2 | * | 3/2011 | Archer et al. .................. 623/62 |

(Continued)

FOREIGN PATENT DOCUMENTS

DE 298648 1/1916
DE 3509879 C2 9/1985

(Continued)

*Primary Examiner* — Thomas J Sweet
*Assistant Examiner* — Jacqueline Woznicki
(74) *Attorney, Agent, or Firm* — Holland & Hart

(57) ABSTRACT

A prosthesis joint including a base, a coupling element for attachment to a body part or a prosthesis section, which is attached to the base, and an attachment device for attachment to a prosthesis device, which is coupled to the base and pivotable around at least one axis. A locking device is coupled to the coupling element and operates to selectively block and enable movement of the attachment device with respect to the base providing locked and unlocked positions, respectively. A retention element is carried by at least one of the base and coupling elements and is elastically pre-stressed against the attachment device to provide a retention force for the attachment device so as to resist undesired pivoting movement.

16 Claims, 5 Drawing Sheets

(56) References Cited

U.S. PATENT DOCUMENTS

2004/0015240 A1* 1/2004 Archer et al. .................. 623/62
2004/0049291 A1* 3/2004 Deharde et al. ................ 623/46
2007/0173955 A1* 7/2007 Archer et al. .................. 623/62
2007/0270976 A1* 11/2007 DeHarde et al. .............. 623/27

FOREIGN PATENT DOCUMENTS

| | | |
|---|---|---|
| DE | 10230655 A1 | 1/2004 |
| GB | 1386942 | 1/1973 |
| WO | 9710781 | 3/1997 |
| WO | 9830177 | 7/1998 |

\* cited by examiner

PROSTHETIC JOINT

CROSS REFERENCE TO RELATED APPLICATION

This patent application claims priority from German Patent Application No. 10 2006 020 777.7 entitled "PROTHESEN-GELENK" filed on May 3, 2006, the entire contents of which are hereby expressly incorporated by reference.

TECHNICAL FIELD

This invention relates to the field of prosthetic appliances, more particularly to the field of prosthetic joints.

BACKGROUND OF THE INVENTION

Prosthetic joints are known which allow two prosthetic parts to swivel relative to one another, and which may be locked with respect to one another. These are generally simple uniaxial joints that may be fixed relative to one another in their respective angular position, optionally in discrete angular increments, by a locking device that blocks the two prosthetic parts. Locking or blocking devices may also be provided for motorized prosthetic devices, in particular to realize energy savings when a prosthetic part must be held in a fixed position under load.

When the lock is released and the distal prosthetic part is in an unlocked state, the part may fall downward due to gravity. This downward drop is generally not controllable, especially for non-motorized prosthetic devices. Thus, for prosthetic hands the problem arises that after the locking device is unlocked, the artificial hand drops downward without damping. This may also occur for forearm prostheses having a prosthetic joint in the elbow region; the situation is analogous for foot or lower-leg prostheses.

SUMMARY OF THE INVENTION

In some embodiments, a prosthetic joint, such as for a hand prosthesis, has a base and a coupling element associated with the base for attaching a body part or to a prosthetic part. A holding device for a prosthetic device, in particular an artificial hand, is connected to the base so as to be pivotable about at least one axis, whereby a locking device blocks the holding device with respect to the base, provides that a retaining element is elastically pretensioned against the holding device and acts upon same with a retention force. This retention force prevents the holding device bearing the distal prosthetic part (for a hand prosthesis, the artificial hand) from swinging downward immediately after the locking device is unlocked.

In particular for hand prostheses, the hand performing the unlocking operation cannot be used to support the artificial hand, since at that time it is occupied with unlocking the locking device. For other applications as well, it may be helpful if the prosthetic part is not rendered powerless immediately after unlocking, but, rather, if the prosthetic part is either held by a retention force in the position in which the unlocking occurred, or only a slow drop against the force of gravity takes place.

In some embodiments, pretensioning of the retaining element may be set in such a way that the holding device, in particular together with the prosthetic device attached thereto, is held in the unlocked position against the force of gravity. In some embodiments, therefore, the retention force is set to be at least equal to the force of gravity, resulting at least in a force equilibrium that prevents motion about the swivel axis. In some embodiments, the retention force is set so that the prosthetic device is just barely held, thus enabling subsequent intentional displacement or swiveling without a great expenditure of force. To allow the retention force to be adjusted when add-on parts or prosthetic devices are exchanged, the pretensioning of the retaining element is adjustable, for example by varying a spring pretension.

In some embodiments, the holding device includes catch elements in which the retaining element engages, the catch elements being designed in such a way that the retaining element or retaining elements are able to slide in and out of the catch elements. The catch elements are used on the one hand for setting discrete angular values, and on the other hand for reducing the pretensioning force necessary to hold the prosthetic device together with the holding device in position. In some embodiments, the catch elements may be designed as recesses, indentations, or projections that are either axially or radially oriented. The orientation depends on the alignment of the retaining element.

In an embodiment, the retaining element is designed as an elastic band, in particular as a round cord, which on the one hand simplifies manufacture and on the other hand allows a sufficiently large retention force while at the same time permitting insertion into and withdrawal from the recesses or indentations.

In another embodiment, the retaining element may also be designed as a dimensionally stable contact part that lies against the holding device and is elastically supported in the direction of the holding device. This is useful when a long service life is desired and consequently only a small amount of abrasion is permitted. Although in a relative motion of an elastic band with respect to the holding device the elastic band wears out fairly quickly, this is prevented by insertion of an elastically supported contact part. In some embodiments, the contact part may be designed as a bearing pin, such as a steel pin, and may lie against the holding device or engage with or contact the recesses, indentations, or projections. In some embodiments, a spring-loaded steel ball may also be used.

The locking device may be designed as a so-called "push-push element" which locks the holding device in a positive-fit manner with respect to the base. Once the locking device is actuated, a positive-fit lock is provided in a specified, discrete position. When the locking device is re-actuated, the positive-fit lock is released and motion against the retention force is made possible by the retaining element. It is likewise provided that the locking device is unlocked by pressing, and is locked by letting go. In that case it is not necessary to re-actuate multiple times.

In some embodiments, especially for a wrist prosthesis, it may be useful for the locking device to be displaceably supported parallel to the swivel axis, thus allowing more or less unnoticeable actuation at the wrist. This actuation is possible essentially independently of the position of the artificial hand relative to the base, since the artificial hand does not limit accessibility in any way.

A prosthesis joint including a base, a coupling element for attachment to a body part or a prosthesis section, which is attached to the base, and an attachment device for attachment to a prosthesis device, which is coupled to the base and pivotable around at least one axis. A locking device is coupled to the coupling element and operates to selectively block and enable movement of the attachment device with respect to the base providing locked and unlocked positions, respectively. A retention element is carried by at least one of the base and coupling elements and is elastically pre-stressed against the attachment device to provide a retention force for the attachment device so as to resist undesired pivoting movement.

DETAILED DESCRIPTION

Figure 1:
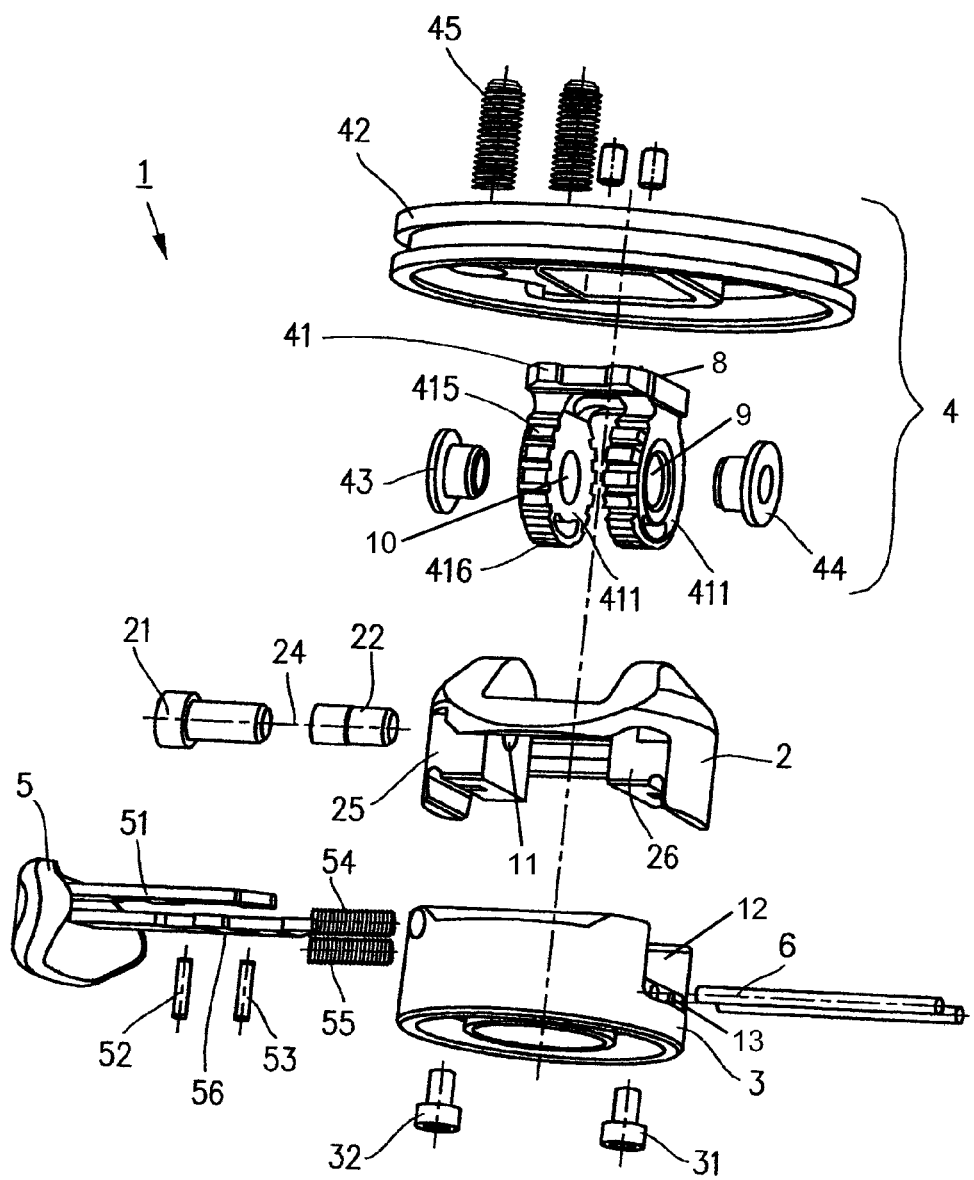
FIG. 1 shows an exploded view of a prosthesis joint according to the present invention.

In FIG. 1 we see an exploded view of a prosthesis joint 1 with a base 2 and a swiveling attachment device 4 which swivels around a swivel axis 24. The attachment device 4 consists of a gear segment piece 41 which has two parallel gear segments 411. These are connected to each other with a bridge 8. Plate 42 is attached to this bridge 8, onto which a further prosthesis part or device can be mounted. For example, an artificial hand (not shown) can be attached to the setscrew or grub screw 45. In the parallel gear segments 411, positioning holes 9, 10 are formed in which bushings 43, 44, such as synthetic bushings, are able to be inserted.

The attachment device 4 is inserted into the base 2 so that the bushings 43, 44 are aligned with the relevant holes 11 in the positioning blocks 25, 26. In addition, bolts 21, 22 extend into the holes 11. The bolts 21, 22 form the running surface for the bushings 43, 44.

In the gear segments 411, recesses 415 and indentations 416 are found (see FIG. 3), whose function and mode of action will be explained as follows.

A locking mechanism or device 5 is located around positioning or bearing blocks 25, 26 and is equipped with locking guides 51 which have protrusions 56 which extend in the direction of the recesses 415 of the gear segments 411.

In the unlocked position, the protrusions 56 in the locking guides 51 are not in contact with the gear segments 411 and extend into the interim space between the gear segments 411, so that each of the gear segments 411 can make contact with the protrusions 56, which insert into the recesses 415, independent of the direction of force of the locking mechanism 5 or the locking guides 51. The locking mechanism moves in a direction parallel with the swivel axis 24 of the attachment device 4 between the locked and unlocked positions (see FIGS. 1 and 2).

Cylinder pins 52, 53 are inserted into the locking guides 51, which are supported on compression springs 54, 55. The compression springs 54, 55 are positioned in a space between the base 2 and a coupling mechanism or element 3. In the coupling mechanism 3 there are holes or guides 12, 13 for a retention element 6, presently two elastic cords or rods, which are generally oriented parallel to the swivel axis 24. The retention element 6 can also be formed from a closed elastic band. In the installed condition the retention element 6 grips the indentations 416 on the side of the gear segment 411 facing away from plate 42 and is elastically supported. The base 2 and the coupling element 3 are connected with two screws 31, 32.

Figure 2:
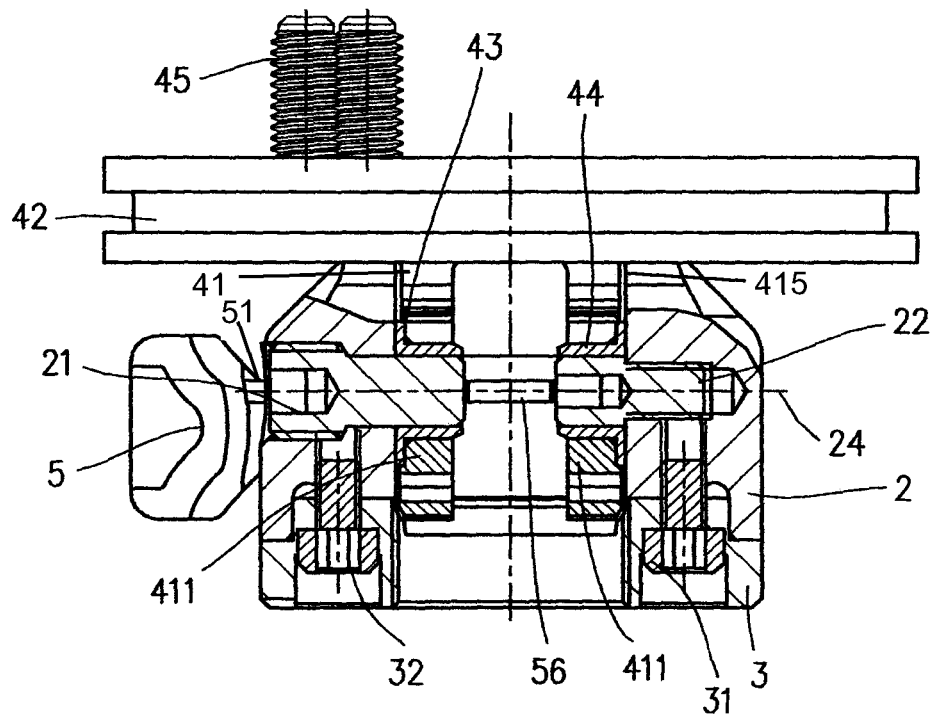
FIG. 2 shows a cutaway view parallel to the swivel axis.

FIG. 2 shows a side view of prosthesis joint 1 in a mounted and locked position. The base 2 is connected to the coupling element 3 with screws 31, 32. The gear segment 41 is screwed or glued to plate 42. In FIG. 2, the position of the bolts 21, 22 in the bushings 43, 44 can be seen within the gear segments 411. The bolts 21, 22 are screwed into the base 2 at the bearing blocks 25, 26. Between the bolts 21, 22 there is free space in which protrusion 56 of the locking guides 51 extends. In FIG. 2, the locked position is shown, in which the protrusion 56 is inserted into a recess 415. Thus, plate 42 is not free to swivel around the swivel axis 24. However, when unlocked, the plate 42 is free to swivel up to ±60° from in the starting position shown.

Figure 3:
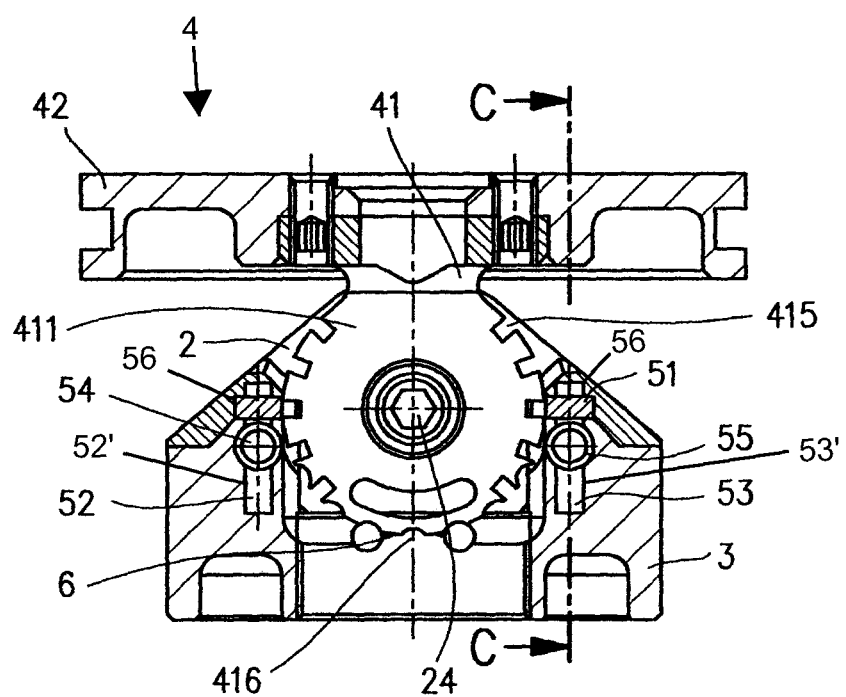
FIG. 3 shows a cutaway view perpendicular to the swivel axis.

FIG. 3 shows a cutaway perpendicular to the swivel axis 24 and shows the interface of the retention element 6 with the indentations 416. The retention element 6 can be made of a pair of elastic staves, rods or of cord. The retention element 6 is pretensioned in the direction of the gear segments 41, in the present model in a radial direction, so that retention force is exerted on the attachment device 4. This retention force is increased by the indentations 416 which are found on the underside of gear segment 411, so that the retention element 6 can be mounted with relatively little pretensioning. Due to the evenly spaced indentations 416 or stop indentations, various stop positions can be set, preferably in even angle intervals. The stop indentations 416 can have the same intervals as the locking recesses 415 and can be positioned in relation to each other, so that in each position of the attachment device 4 in the unlocked mode, locking can occur through axial movement of the locking mechanism 5 (not illustrated in this view). In one aspect, the locking mechanism 5, of the present invention, includes an element that engages the attachment device 4 with a positive fit.

Free spaces 52', 53' can be identified in FIG. 3, in which the cylinder pins 52, 53 are movable. The cylinder pins 52, 53 are acted upon via compression springs 54, 55 with a retention force, so that the locking mechanism 5 is always spring loaded in one direction. In the starting position, the locking mechanism 5 is in the locked position and is held there. In the locked position, there is a fixing of the attachment device 4 by the interface or engagement of the protrusions 56 into the locking recesses 415. If pressure is introduced against the spring force, the protrusions 56 are moved out of the locking recesses 415 and enable a swing or pivoting of the attachment device 4, or the artificial hand attached to it, around the swivel axis 24. If the locking mechanism 5 is released, it springs back due to the retention force of the compression springs 54, 55 and brings the protrusions 56 back into interface or engagement with the locking recesses 415.

An alternative can be a so called push-push-element, which is returned to the starting position after being twice activated.

Figure 4:
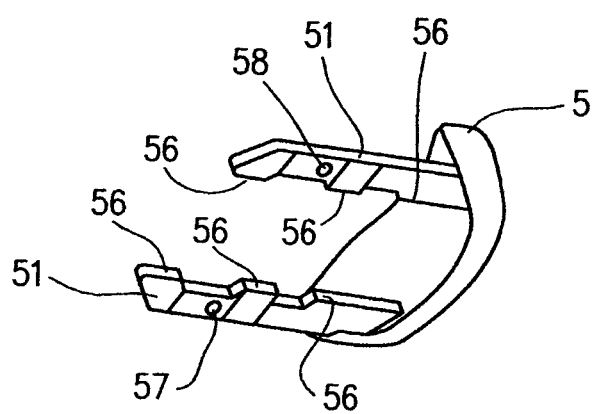
FIG. 4 shows an individual view of a locking mechanism.

FIG. 4 shows a locking mechanism 5 with the locking guides 51 and the protrusions 56 in individual views. The cylinder pins 52, 53 (not shown in this view) can be inserted into the holes 57, 58.

An alternative to the design illustrated, with a direct coupling of an elastic retention element 6 with the gear segments 41 and/or the attachment device 4, can be a contact part of a hard or abrasion resistant material between an elastic element and the gear segments 41 and/or the indentations 416. Through this, the sliding of the retention element 6 or contact parts is made easier on one hand, and on the other hand, the life of the prosthesis is increased.

It is also possible to have an axial retention force, instead of a radial effective retention force. For example, there can be stop recesses or protrusions in recesses in the side surface of the gear segments 41, which interface with the retention elements. For example, a spring loaded bearing could interface into a calotte-shaped recess.

Due to the prosthesis joint of the current invention, an uncontrolled falling of a prosthesis device after unlocking is hindered without affecting adjustability. It can be arranged so that the stop elements are removed from engagement, so that a spontaneous change in position is possible without additional adjustment force. It is also basically possible to set the pre-tension and therefore the retention force to the personal wishes of the wearer and to be able to adjust it for changing situations.

The prosthesis joint can either be attached to a body part or to another prosthesis section, such as onto a lower arm prosthesis.

In addition to the use as a prosthetic wrist, other joint elements can be effected, such as knee or elbow joints. It may also be used in motor driven prostheses in order to reduce energy consumption. The retention force in the unlocked position can be selected to be so slight that the drive must only provide a slightly higher output. This additional expenditure is compensated for by removing the need of using the motor to hold prosthesis devices. The control of the drive can occur via myoelectrical signals.

Figure 5:
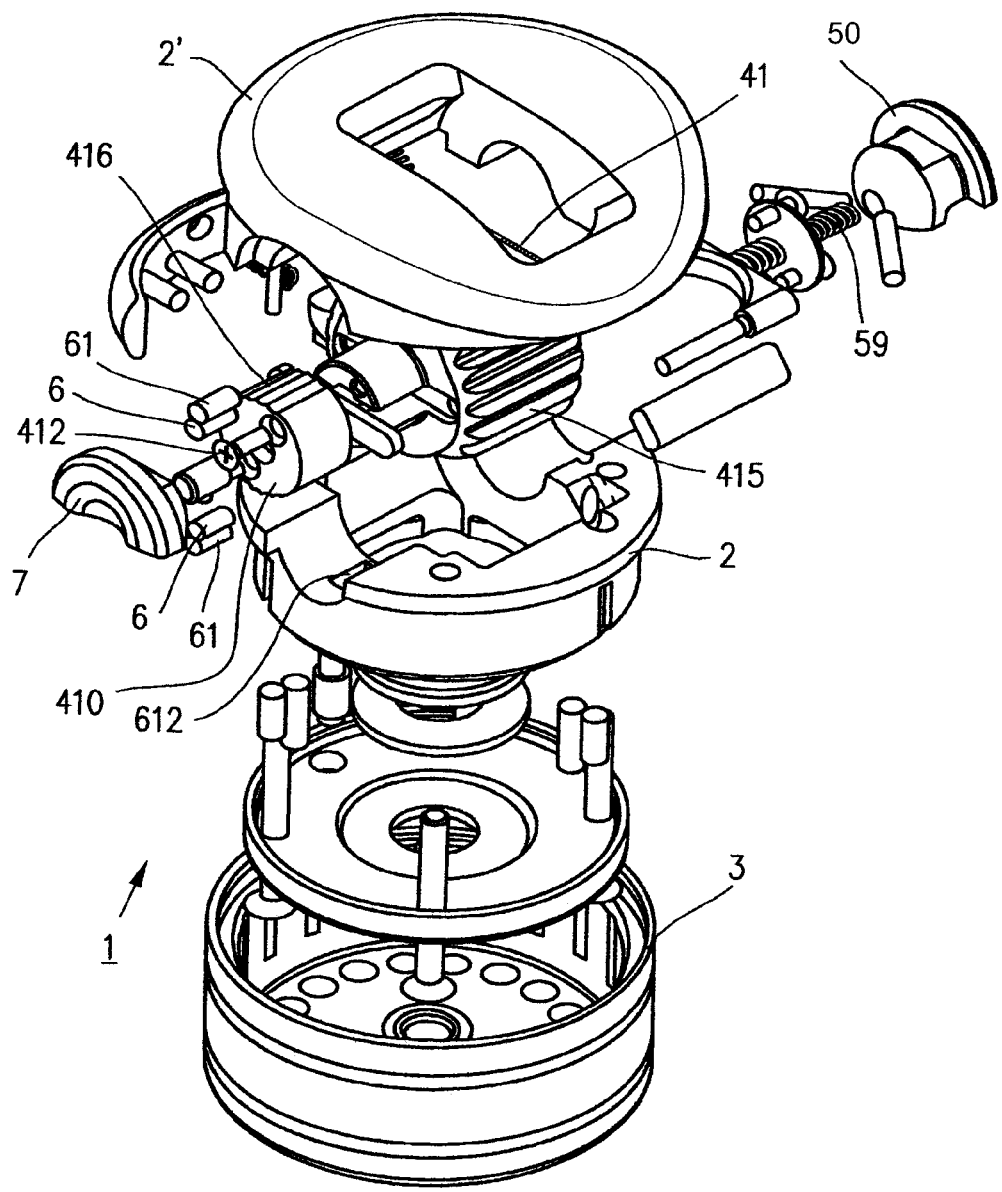
FIG. 5 shows an exploded view of an alternative embodiment of the prosthetic joint of the present invention.

In another embodiment, like components have the same reference number as those in the first embodiment. FIG. 5 shows a variant of prosthesis 1 in an exploded view which shows the retention element 6 as steel pins. These pins 6 are pre-tensioned over an elastic strap 61 or an elastic element against a bushing 410, which loads this retention element 6 with retention force. The bushing 410 is connected with the gear segment part 41 with screws 412 and transfers the radial retention force from the bushing 410 to the attachment device 4. The two part configuration of the retention element 6, in the form of steel pins, and an elastic element 61, provides increased retention and minimization of wear and tear.

The elastic strap 61 and/or another elastic element is positioned in the recess 612, of which only one is shown, in base 2. Accordingly, an additional recess is located in the upper section 2' of base 2. In this aspect, the present invention may be seen to include a retention element 6 as a dimensionally stable contact part which abuts the attachment device 4 and is elastically positioned in a direction towards and away from the attachment device 4.

The bushing 410 is also made of steel, just as the retention element 6, in order to produce an abrasion minimizing materials pairing. Alternatives could also be indentations 416 formulated directly on the gear segment part 41.

Figure 6:
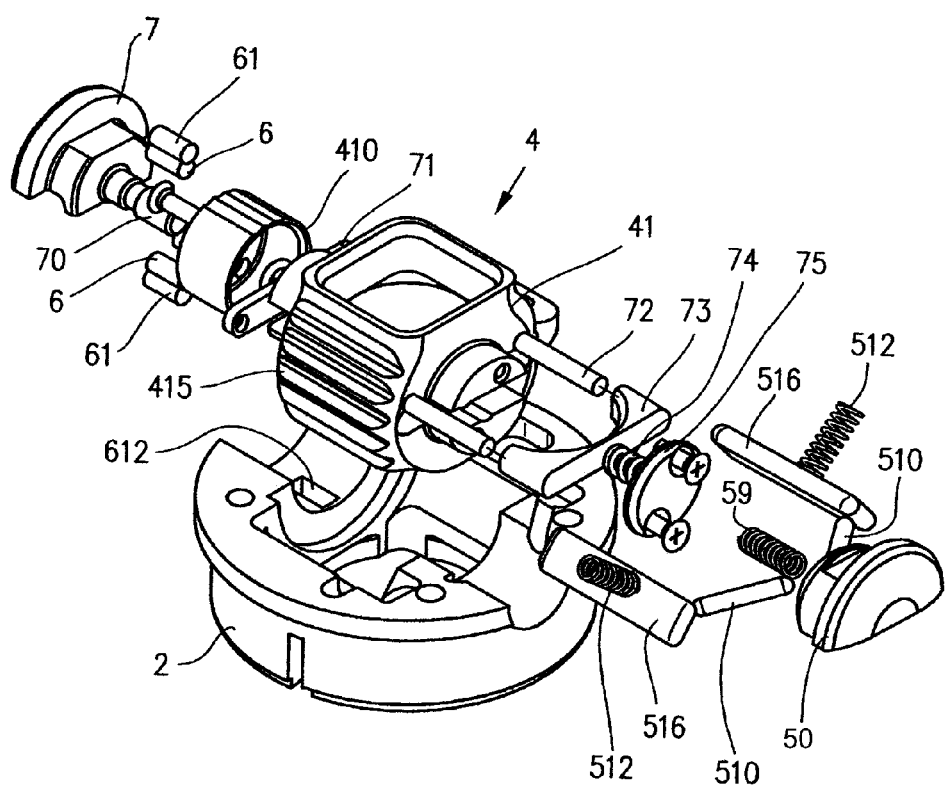
FIG. 6 shows a detail view of a portion of FIG. 5.

FIG. 6 shows the prosthesis joint 1, pursuant to FIG. 5, in a detail view without upper section 2' of base 2. One can see that the gear segment part 41 is made of a single piece and, in addition, forms the attachment device 4 for a coupling element for the prosthetic hand (not shown). A locking and unlocking mechanism 5 enables a quick and easy locking and unlocking of an adaptor for a artificial hand in the attachment device 4 mechanism gear segment 41. The locking of the attachment device 4 against a swivel or pivoting movement occurs via the locking device 5 made up of bars 516. Bars 516 can be pivoted out of the preset interface or engagement position via pins 510 with a retention force provided by springs 512. The bars 516 are positioned in the base 2 and are spring loaded. The pins 510 abut a spherical actuation surface for the locking device 5. The locking device 5 is primarily designed as a pressure button and is held in the starting position, in which the bars 516 interface with the locking recesses 415, via a compression spring 59. If the button 50 is pressed, the pins 510 will be pressed against the bars 516 by the spring force and will move them out of contact. When the button 50 is released, there is a reverse movement.

For the quickest locking and unlocking of the artificial hand with the attachment device 4, as with a quick-connect feature, an additional pressure button 7 is added, which reaches over an axis 70 through the bushing 410 and is coupled with a force transfer element 71. This force transfer element 71 is coupled with a key element 73 via pins 72, which is movable and positioned in the attachment device 4 with spring force of a spring 74 acting against element 75 which is secured to piece 41. If the button 7 is actuated, the key element 73 is moved by the force of spring 74 in the direction of the screwed in thrust bearing and does not release the artificial hand. To lock the artificial hand, button 7 is held in, whereby the attachment device 4 is prepared for the insertion of the adaptor of an artificial hand. After pressing and releasing the button 7, the adapter is automatically locked due to the retention force of spring 74. This also provides that the adapter be inserted into the attachment device 4, which moves the key element 73 on its own and finally locks it into the attachment device 4.

In one aspect, the present invention provides pre-stressing of the retention element by an amount sufficient to hold the attachment device in the unlocked position against the force of gravity.

The invention claimed is:

1. A prosthesis joint comprising:
a base;
a coupling element coupled to the base and configured for attaching the base to a body part or another prosthesis component attached to the body part;
an attachment device attached to the base and configured for attaching the base to a prosthesis device, the attachment device pivotable around at least one axis, the attachment device including a gear element having a circumference and a plurality of recesses formed at one location around the circumference of the gear element and a plurality of indentations formed at another location around the circumference of the gear element;
a locking device coupled to the coupling element and operative to selectively block and enable pivoting movement of the attachment device with respect to the base, providing locked and unlocked positions, respectively, the locking device including locking guides that engage the gear element recesses in the locked position creating stop positions and disengage from the gear element recesses in the unlocked position; and
a retention element coupled to at least one of the base and coupling element, the retention element elastically pre-stressed against the gear element to provide a retention force for the attachment device so as to resist pivoting movement, the retention device including at least one elastic cord or rod that engages at least one of the plurality of indentations, gripping the gear element,
wherein the indentations are aligned with the recesses, such that the attachment device resists pivoting movement when the locking device is unlocked at the stop positions; and
wherein the pre-stressing of the retention element is sufficient to prevent pivoting of the attachment device by the force of gravity when the locking device is in the unlocked position.

2. The prosthesis joint of claim 1, wherein the attachment device has rest elements to which the retention element can grip.

3. The prosthesis joint of claim 2, wherein the rest elements are formed as the plurality of indentations.

4. The prosthesis joint of claim 1, wherein the at least one retention element is a plurality of elastic cords or rods.

5. The prosthesis joint of claim 1, wherein the at least one retention element is an elastic band.

6. The prosthesis joint of claim 1, wherein the locking device includes an element that engages the attachment device with a positive fit.

7. The prosthesis joint of claim 1, wherein the locking device is positioned parallel to the axis in a moveable manner.

8. The prosthesis joint of claim 1, wherein the locking device is moveable relative to a spring force, such that movement of the locking device against the spring force results in disengagement from the attachment device and release of the locking device and spring force results in engagement with the attachment device.

9. The prosthesis joint of claim 1, wherein stop positions are distributed over an angular range of pivoting movement of the attachment device, the stop positions providing the locked positions at predetermined angles with respect to the base.

10. The prosthesis joint of claim 9, wherein the attachment device comprises rest elements to which the retention element can contact and wherein the rest elements are aligned with the stop positions of the locking device, such that the attachment device resists pivoting movement when the locking device is unlocked at the stop positions.

11. A prosthesis comprising the prosthesis joint of claim 1, wherein a prosthetic hand is attached to the attachment device.

12. A prosthesis comprising the prosthesis joint of claim 1, wherein a prosthesis component is coupled to the coupling element.

13. A prosthesis comprising the prosthesis joint of claim 1, wherein the locking device operates in a direction parallel with a rotation axis of the gear element to engage and disengage from the gear element.

14. A prosthesis joint comprising:
a base;
a coupling element coupled to the base and configured for attaching the base to a body part or another prosthesis component attached to the body part;
an attachment device attached to the base and configured for attaching the base to a prosthesis device, the attachment device pivotable around at least one axis, the attachment device including a gear element having a circumference and a plurality of recesses formed at one location around the circumference of the gear element and a plurality of indentations formed at another location around the circumference of the gear element;
a locking device coupled to the coupling element and operative to selectively block and enable pivoting movement of the attachment device with respect to the base, providing locked and unlocked positions, respectively, the locking device including locking guides that engage the gear element recesses in the locked position creating stop positions and disengage from the gear element recesses in the unlocked position; and
a retention element coupled to at least one of the base and coupling element, the retention element elastically pre-stressed against the gear element to provide a retention force for the attachment device so as to resist pivoting movement, the retention device including a pair of elastic cords or rods that engage a pair of the plurality of indentations, gripping the gear element,
wherein the indentations are aligned with the recesses, such that the attachment device resists pivoting movement when the locking device is unlocked at the stop positions; and
wherein the pre-stressing of the retention element is sufficient to prevent pivoting of the attachment device by the force of gravity when the locking device is in the unlocked position.

15. A prosthesis joint comprising:
a base;
a coupling element coupled to the base and configured for attaching the base to a body part or another prosthesis component attached to the body part;
an attachment device attached to the base and configured for attaching the base to a prosthesis device, the attachment device pivotable around at least one axis, the attachment device including a gear element having a circumference and a plurality of recesses formed at one location around the circumference of the gear element and a plurality of indentations formed at another location around the circumference of the gear element;
a locking device coupled to the coupling element and operative to selectively block and enable pivoting movement of the attachment device with respect to the base, providing locked and unlocked positions, respectively, the locking device including locking guides that engage the gear element recesses in the locked position creating stop positions and disengage from the gear element recesses in the unlocked position; and
a retention element coupled to at least one of the base and coupling element, the retention element elastically pre-stressed against the gear element to provide a retention force for the attachment device so as to resist pivoting movement, the retention device including a plurality of elastic cords or rods that engage a plurality of indentations, gripping the gear element,
wherein the indentations are aligned with the recesses, such that the attachment device resists pivoting movement when the locking device is unlocked at the stop positions; and
wherein the pre-stressing of the retention element is sufficient to prevent pivoting of the attachment device by the force of gravity when the locking device is in the unlocked position.

16. A prosthesis joint comprising:
a base;
a coupling element coupled to the base and configured for attaching the base to a body part or another prosthesis component attached to the body part;
an attachment device attached to the base and configured for attaching the base to a prosthesis device, the attachment device pivotable around at least one axis, the attachment device including a gear element having a circumference and a plurality of recesses formed at one location around the circumference of the gear element and a plurality of indentations formed at another location around the circumference of the gear element;
a locking device coupled to the coupling element and operative to selectively block and enable pivoting movement of the attachment device with respect to the base, providing locked and unlocked positions, respectively, the locking device including locking guides that engage the gear element recesses in the locked position creating stop positions and disengage from the gear element recesses in the unlocked position; and
a retention element coupled to at least one of the base and coupling element, the retention element elastically pre-stressed against the gear element to provide a retention force for the attachment device so as to resist pivoting movement, the retention device including at least one elastic member that engages at least one of the plurality of indentations, gripping the gear element, wherein the indentations are aligned with the recesses, such that the attachment device resists pivoting movement when the locking device is unlocked at the stop positions; and wherein the pre-stressing of the retention element is sufficient to prevent pivoting of the attachment device by the force of gravity when the locking device is in the unlocked position.

* * * * *